US011110163B2

(12) United States Patent
Kapre et al.

(10) Patent No.: US 11,110,163 B2
(45) **Date of Patent: *Sep. 7, 2021**

(54) HEAT STABLE VACCINES

(71) Applicant: Inventprise, LLC, Redmond, WA (US)

(72) Inventors: Subhash V. Kapre, Redmond, WA (US); Ivan A. Olave, Kirkland, WA (US)

(73) Assignee: Inventprise, LLC, Redmond, WA (US)

(*) Notice: Subject to any disclaimer, the term of this patent is extended or adjusted under 35 U.S.C. 154(b) by 18 days.

This patent is subject to a terminal disclaimer.

(21) Appl. No.: 16/571,702

(22) Filed: Sep. 16, 2019

(65) Prior Publication Data
US 2020/0009242 A1 Jan. 9, 2020

Related U.S. Application Data

(63) Continuation-in-part of application No. 15/896,939, filed on Feb. 14, 2018, now Pat. No. 10,413,604.

(60) Provisional application No. 62/458,904, filed on Feb. 14, 2017.

(51) Int. Cl.

| | |
|---|---|
| *A61K 39/15* | (2006.01) |
| *A61K 47/18* | (2017.01) |
| *A61K 47/26* | (2006.01) |
| *A61K 47/14* | (2017.01) |
| *C12N 7/00* | (2006.01) |
| *A61K 9/19* | (2006.01) |
| *A61K 39/00* | (2006.01) |

(52) U.S. Cl.

CPC ................ *A61K 39/15* (2013.01); *A61K 9/19* (2013.01); *A61K 47/14* (2013.01); *A61K 47/183* (2013.01); *A61K 47/26* (2013.01); *C12N 7/00* (2013.01); *A61K 2039/5254* (2013.01); *C12N 2720/12334* (2013.01)

(58) Field of Classification Search
CPC ...... A61K 39/15; A61K 47/183; A61K 47/26; A61K 47/14; A61K 9/19; A61K 2039/5254; A61K 39/12; A61K 9/0053; A61K 9/0095; A61K 9/10; A61K 9/1611; A61K 9/1682; A61K 9/1623; A61K 2039/542; A61K 2039/525; C12N 7/00; C12N 2720/12334; C12N 2720/12321; A61P 31/14

See application file for complete search history.

(56) References Cited

U.S. PATENT DOCUMENTS 6,616,931 B1 9/2003 Burke
6,651,655 B1 11/2003 Licalsi ............. A61M 15/0028 128/203.15
8,241,886 B2 8/2012 Truong-Le et al.
2011/0177119 A1 7/2011 Dhere et al.
2014/0242113 A1 8/2014 Ruiz

FOREIGN PATENT DOCUMENTS

WO WO 2001/08495 2/2001
WO WO 2002/011540 2/2002
WO WO 2007/056847 5/2007
WO WO 2007/132480 11/2007
WO WO 2016/009381 1/2016
WO WO 2016/009400 1/2016
WO WO-2016009381 A2 1/2016 ............ A61K 39/12

OTHER PUBLICATIONS

Tamilvanan, S. (2010). Progress in Design of Biodegradable Polymer-Based Microspheres for Parenteral Controlled Delivery of Therapeutic Peptide/Protein. In Pharmaceutical Sciences Encyclopedia, S.C. Gad (Ed.). https://doi.org/10.1002/9780470571224.pse351.*
Chen J. Fabrication, Characterization and Biological Fate of Phytochemical Delivery System. Doctoral Dissertation, Nov. 2015. Univ. of Massachusetts at Amherst.*
Malenovská H. The influence of stabilizers and rates of freezing on preserving of structurally different animal viruses during lyophilization and subsequent storage. J Appl Microbiol. Dec. 2014;117(6):1810-9. Epub Nov. 4, 2014.*
Croyle MA, Cheng X, Wilson JM. Development of formulations that enhance physical stability of viral vectors for gene therapy. Gene Ther. Sep. 2001;8(17):1281-90.*
Fox CB, Baldwin SL, Duthie MS, Reed SG, Vedvick TS. Immunomodulatory and physical effects of oil composition in vaccine adjuvant emulsions. Vaccine. Nov. 28, 2011;29(51):9563-72. Epub Sep. 9, 2011.*
Hansen LJJ, Daoussi R, Vervaet C, Remon JP, De Beer TRM. Freeze-drying of live virus vaccines: A review. Vaccine. Oct. 13, 2015;33(42):5507-5519. Epub Sep. 26, 2015. (Year: 2015).*
Lovalenti PM, Anderl J, Yee L, Nguyen V, Ghavami B, Ohtake S, Saxena A, Voss T, Truong-Le V. Stabilization of Live Attenuated Influenza Vaccines by Freeze Drying, Spray Drying, and Foam Drying. Pharm Res. May 2016;33(5):1144-60. Epub Jan. 27, 2016. (Year: 2016).*
Alcock R, Cottingham MG, Rollier OS, Furze J, De Costa SD, Hanlon M, Spencer AJ, Honeycutt JD, Wyllie DH, et al. Long-term thermostabilization of live poxviral and adenoviral vaccine vectors at supraphysiological temperatures in carbohydrate glass. Sci Transl Med. Feb. 17, 2010;2(19):19ra12. (Year: 2010).*
University of Washington, Dept. of Global Health. Interactive World Map. Projects: Inventprise: Stabilization of Live Rotavirus Vaccine. Jul. 1, 2013. Accessed Aug. 3, 2019. https://globalheath.washington.edu/interactive-map/projects/2591/Inventprise-Stabilization-of-live-rotavirus-vaccine-.

(Continued)

*Primary Examiner* — Rachel B Gill
(74) *Attorney, Agent, or Firm* — Remenick PLLC

(57) ABSTRACT

The invention is directed to an oral vaccine composed of a micronized freeze-dried rotavirus particle suspension with buffering excipients in a non-aqueous liquid. This IVT-06 formulation has imparted heat stability by protecting the virus at temperatures of 30° C. and 40° C. for at least twelve months. Extrapolations from the 12-month stability data indicate a shelf life of more than two years at 30° C., and six months at 50° C. In addition, for ease of administration, the formulated dose has a volume of 0.5 mL.

36 Claims, 12 Drawing Sheets

(56) References Cited

OTHER PUBLICATIONS

Figure 1:
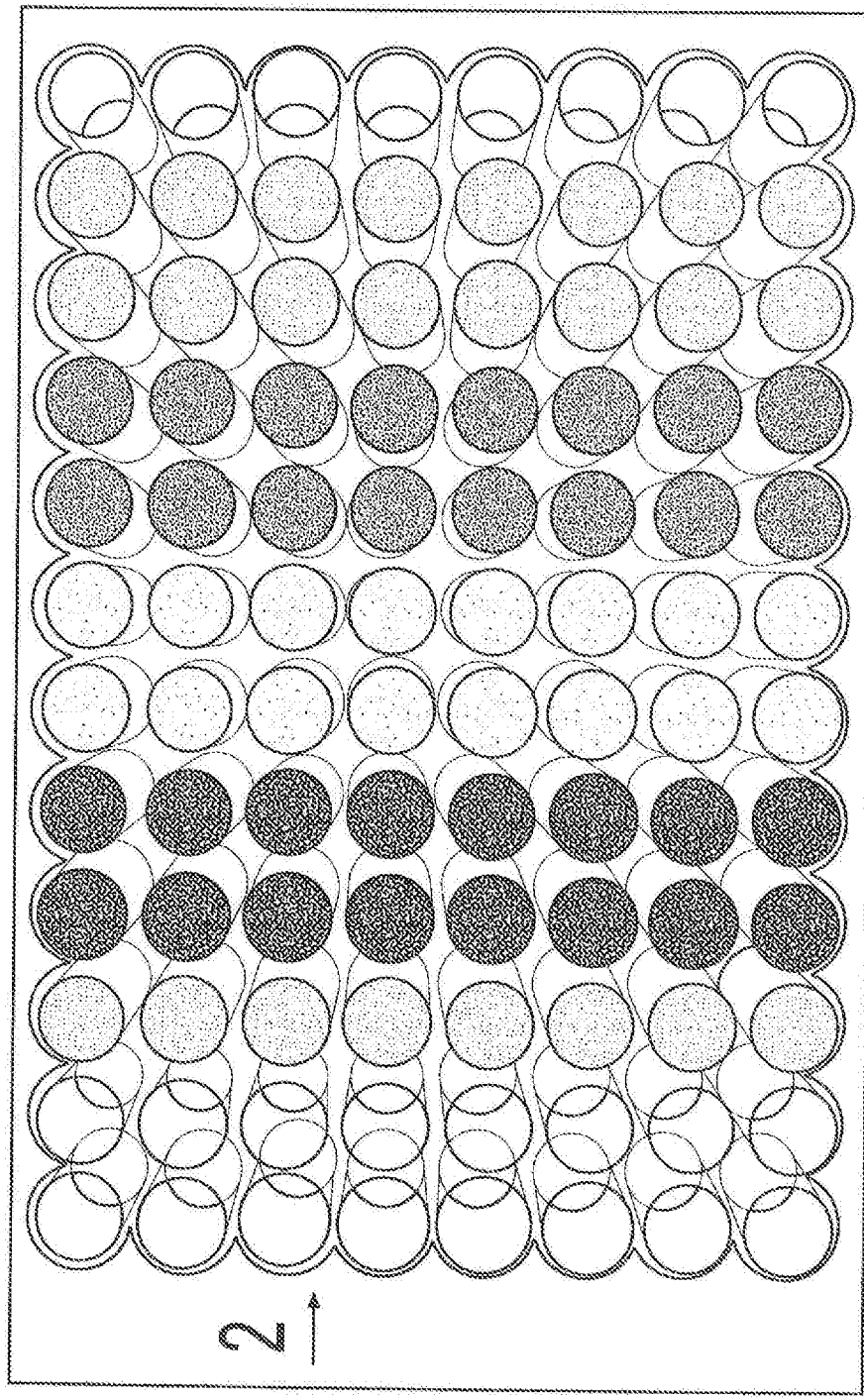

Naik SP, Zade JK, Sabale RN, Pisal SS, Menon R, Bankar SG, Gairola S, Dhere RM. Stability of heat stable, live attenuated Rotavirus vaccine (ROTASIIL®). Vaccine. May 19, 2017;35(22):2962-2969. doi: 10.1016/j.vaccine.2017.04.025. Epub Apr. 20, 2017.

Pastorino B, Baronti C, Gould EA, Charrel RN, de Lamballerie X. Effect of chemical stabilizers on the thermostability and infectivity of a representative panel of freeze dried viruses. PLoS One. Apr. 29, 2015;10(4):e0118963. doi: 10.1371/journal.pone.0118963. eCollection 2015.

Barley J. "Basic Principles of Freeze Drying". https://www.spscientific.com/freeze-drying-lyophilization-basics/. Accessed Apr. 19, 2019.

Third Part Observations of PCT/US2018/18226 dated Dec. 22, 2018 (Part 1).

Third Part Observations of PCT/US2018/18226 dated Dec. 22, 2018 (Part 2).

Liu C, Yang S, Liu W, Wang R, Wan J, Li W. Preparation and characterization of medium-chain fatty acid liposomes by lyophilization. J Liposome Res. Sep. 2010;20(3):183-90.

Alkeev N, Averin S, von Gratowiski S. New Method for Monitoring the Process of Freeze Drying of Biological Materials. AAPS PharmSciTech. Dec. 2015;16(6):1474-9. Epub May 29, 2015.

Search Report and Preliminary Written Opinion of PCT/US2018/18226 dated Apr. 27, 2018.

Examination Report for KR Application No. 10-2019-7026145 dated Jan. 26, 2021.

Examination Report for KR Application No. 10-2019-7026145 dated Jan. 26, 2021—translated.

E.L. Parrott, Journal of Pharmaceutical Sciences; vol. 63 No. 6; pp. 813-829; Jun. 1974.

\* cited by examiner

| FORMULATION | TIME @ 40C | MEASURED TITER | | |
|---|---|---|---|---|
| | SAMPLE NAME | (FFU/mL) | LOG10 | Loss to t = 0 |
| IVT-00 | t = 0 | 4.30E+03 | 3.63 | 0.00 |
| | 1 WEEK | 2.60E+03 | 3.41 | -0.22 |
| | 2 WEEK | 2.70E+03 | 3.43 | -0.20 |
| IVT-01 | t = 0 | 1.30E+04 | 4.12 | 0.00 |
| | 1 MONTH | 1.50E+03 | 3.17 | -0.95 |
| | 2 MONTHS | 5.10E+02 | 2.71 | -1.41 |

*FIG. 2*

| BATCH # | % MOISTURE | TIME AT 40C DEGREES | MEASURED TITER* | | |
|---|---|---|---|---|---|
| | | | (FFU/mL) | LOG10 | Loss to t = 0 |
| BATCH 1 | 2.73% | t = 0, AVERAGE n = 6 | 8.20E+04 | 4.91 | 0 |
| | | 1 MONTH | 6.10E+04 | 4.78 | -0.13 |
| | | 2 MONTHS | 2.80E+04 | 4.45 | -0.46 |
| | | 4 MONTHS | 8.40E+03 | 3.92 | -0.99 |
| | | 6 MONTHS | 2.40E+03 | 3.38 | -1.53 |
| BATCH 2 | 2.55% | t = 0, AVERAGE n = 6 | 9.11E+04 | 4.96 | 0 |
| | | 1 MONTH | 4.80E+04 | 4.68 | -0.28 |
| | | 3 MONTHS | 2.39E+04 | 4.38 | -0.58 |
| | | 4 MONTHS | 3.04E+04 | 4.48 | -0.48 |
| | | 6 MONTHS | 2.87E+03 | 3.46 | -1.50 |
| BATCH 6B | 1.44% | t = 0 | 1.73E+05 | 5.24 | 0 |
| | | 4 MONTHS | 7.79E+04 | 4.89 | -0.35 |
| BATCH 6C | 1.28% | t = 0, AVERAGE n = 2 | 1.11E+05 | 5.04 | 0 |
| | | 1 MONTH | 7.87E+04 | 4.90 | -0.14 |
| | | 4 MONTHS | 5.73E+04 | 4.76 | -0.28 |
| | | 6 MONTHS | 3.2E+04 | 4.51 | -0.33 |

FIG. 4

| TEMP [C] | TIME [MONTH] | IVT-05 | | | IVT-06 WITH 2% ARGININE | | | IVT-06 WITH 4% ARGININE | | |
|---|---|---|---|---|---|---|---|---|---|---|
| | | TITER* [FFU/mL] | LOG10 | LOSS TO t = 0 | TITER* [FFU/mL] | LOG10 | LOSS TO t = 0 | TITER* [FFU/mL] | LOG10 | LOSS TO t = 0 |
| 30C | T = 0 | 2.81E+04 | 4.45 | NA | 3.25E+04 | 4.51 | NA | 2.35E+04 | 4.37 | NA |
| 30C | 1 | 2.32E+04 | 4.37 | -0.08 | 2.82E+04 | 4.45 | -0.06 | 1.71E+04 | 4.23 | -0.14 |
| 30C | 2 | 2.56E+04 | 4.41 | -0.04 | 2.96E+04 | 4.47 | -0.04 | 9.10E+03 | 3.96 | -0.41 |
| 30C | 3 | 1.58E+04 | 4.20 | -0.25 | 2.5E+04 | 4.40 | -0.11 | 2.7E+04 | 4.43 | +0.06 |
| 30C | 6 | 2.79E+04 | 4.45 | 0.00 | 4.43E+04 | 4.65 | +0.13 | 2.21E+04 | 4.34 | -0.03 |
| 30C | 8 | NA | NA | NA | NA | NA | NA | 4.65E+04 | 4.67 | +0.30 |
| 30C | 12 | 1.45E+04 | 4.16 | -0.29 | 1.82E+04 | 4.26 | -0.25 | 1.73E+04 | 4.24 | -0.13 |

*FIG. 5*

| TEMP [C] | TIME [MONTH] | IVT-05 | | | IVT-06 | | | IVT-06 WITH 2% ARGININE | | | IVT-06 WITH 4% ARGININE | | |
|---|---|---|---|---|---|---|---|---|---|---|---|---|---|
| | | TITER* [FFU/mL] | LOG10 | LOSS TO t=0 | TITER* [FFU/mL] | LOG10 | LOSS TO t=0 | TITER* [FFU/mL] | LOG10 | LOSS TO t=0 | | | |
| S40C | T=0 | 2.81E+04 | 4.45 | NA | 3.25E+04 | 4.51 | NA | 2.35E+04 | 4.37 | NA | | | |
| 40C | 1 | 2.58E+04 | 4.41 | -0.04 | 5.37E+04 | 4.73 | +0.22 | 5.37E+04 | 4.73 | +0.36 | | | |
| 40C | 3 | 3.58E+04 | 4.55 | +0.10 | 6.65E+04 | 4.82 | +0.31 | 6.65E+04 | 4.82 | +0.45 | | | |
| 40C | 6 | 2.61E+04 | 4.42 | -0.03 | 4.43E+04 | 4.65 | +0.13 | 4.43E+04 | 4.65 | +0.28 | | | |
| 40C | 8 | 1.47E+04 | 4.17 | -0.28 | NA | N/A | N/A | 2.6E+04 | 4.42 | +0.05 | | | |
| 40C | 12 | 7.07E+03 | 3.85 | -0.60 | 9.33E+03 | 3.97 | -0.54 | 1.94E+04 | 4.29 | -0.08 | | | |

FIG. 6

| TEMP [C] | TIME [MONTH] | IVT-05 | | | IVT-06 WITH 2% ARGININE | | | IVT-06 WITH 4% ARGININE | | |
|---|---|---|---|---|---|---|---|---|---|---|
| | | TITER* [FFU/mL] | LOG10 | LOSS TO t = 0 | TITER* [FFU/mL] | LOG10 | LOSS TO t = 0 | TITER* [FFU/mL] | LOG10 | LOSS TO t = 0 |
| 50C | T = 0 | 2.81E+04 | 4.45 | NA | 3.25E+04 | 4.51 | NA | 2.35E+05 | 4.37 | NA |
| 50C | 1 | 1.79E+04 | 4.254 | -0.20 | 1.52E+04 | 4.18 | -0.33 | 1.11E+04 | 4.04 | -0.33 |
| 50C | 2 | 2.05E+04 | 4.31 | -0.14 | 7.03E+03 | 3.85 | -0.67 | 1.41E+04 | 4.15 | -0.22 |
| 50C | 3 | 2.1E+03 | 3.32 | -1.13 | 1.0E+04 | 4.01 | -0.50 | 1.42E+04 | 4.15 | -0.22 |

FIG. 7

| MONTHS | EXPECTED TITER LOG$_{10}$ [FFU/mL] IN IVT-06 | |
| --- | --- | --- |
| | AT 30°C | AT 50°C |
| 0 | 5.600 | 5.600 |
| 1 | 5.599 | 5.499 |
| 2 | 5.599 | 5.397 |
| 3 | 5.598 | 5.296 |
| 4 | 5.598 | 5.194 |
| 5 | 5.597 | 5.093 |
| 6 | 5.596 | 4.991 |
| 9 | 5.595 | |
| 12 | 5.593 | |
| 15 | 5.591 | |
| 18 | 5.589 | |
| 21 | 5.587 | |
| 24 | 5.586 | |

*FIG. 10*

| EXPECTED TITER $LOG_{10}$ [FFU/mL] IN IVT-06 AT 50°C | | |
|---|---|---|
| MONTHS | WITH 2% ARGININE | WITH 4% ARGININE |
| 0 | 5.60 | 5.60 |
| 1 | 5.38 | 5.49 |
| 2 | 5.15 | 5.39 |
| 3 | 4.93 | 5.28 |
| 4 | 4.70 | 5.18 |
| 5 | 4.48 | 5.07 |
| 6 | 4.25 | 4.97 |
| 7 | 4.03 | 4.86 |

HEAT STABLE VACCINES

REFERENCE TO RELATED APPLICATIONS

This application is a continuation-in-part of U.S. application Ser. No. 15/896,939 filed Feb. 14, 2018, which issued as U.S. Pat. No. 10,413,604 on Sep. 17, 2019, and claims priority to U.S. Provisional Application No. 62/458,904 of the same title filed Feb. 14, 2017, the entirety of each of which is specifically incorporated by reference.

BACKGROUND

1. Field of the Invention

The present invention provides compounds, compositions, vaccines and methods for the treatment and prevention of viral infections and, in particular, oral vaccines and formulations that are stable and effective at room temperatures and higher for long periods of time.

2. Description of the Background

Rotavirus infection is the leading cause of severe diarrheal diseases in infant and young children (Kotloff et al., 2013). Until 2008, before the introduction universal rotavirus immunization programs, diarrheal diseases accounted for 37% of all mortality among infants and children under 5 years of age, with an estimated burden of near half a million deaths a year (Tate el al., 2008; Kotloff et al., 2013). Most of this mortality occurred in poor countries.

There are nine species of rotavirus, referred to as A, B, C, D, E, F, G, H, and I. Humans are primarily infected by species A, B and C, most commonly by species A. A-E species cause disease in other animals, species E and H in pigs, and D, F and G in birds. Within rotavirus A there are multiple serotype (also referred to as strains). The classification system used is based on the two major surface proteins, VP7, a glycoprotein that defines the G serotypes, VP4 which defines P serotypes. Genes that determine G-types and P-types are passed along separately to progeny viruses and many combinations have been identified.

Since 2006 three oral live attenuated rotavirus vaccines —ROTATEQ from Merck, ROTARIX from Glaxo SmithKline, and ROTAVAC from Bharat Biotech became available in the market to help preventing severe rotavirus infections. (Vesikari et al., 2006, & 2007; Bhandari et al., 2014a, b). Dose have from $1$-$2.8 \times 10^6$ $CCID_{50}$ per dose.

Two of these vaccines are available in liquid formulations of 1.5-2.0 mL and are required to be stored at 2-8° C. (cold chain storage); while the third one is a frozen formulation requiring freezer storage at all times to preserve rotavirus stability and therefore, maintain their efficacy. According to package inserts, administration of the vaccine is required as soon as possible after removal from refrigeration. (Matthias, 2007). In addition, establishing a cold chain system is expensive, requires large amounts of space, and a big organization and infrastructure that sometimes is difficult to execute in poor countries that need the most help in prevention.

The moment that the cold chain becomes unnecessary right from the manufacturer site, cold storage space for the vaccine and their cold packing materials also becomes irrelevant. In addition, a dose volume reduction would make the footprint for storage and delivery of vaccines much smaller, with the additional benefit of allowing the preparation of a vaccine multi-dose form, similar to those currently used for the oral polio vaccine. Also in the field the dose volume of oral polio is well established which is 0.5 ml or lower.

A product prepared as lyophilized needs to have an accompaniment of buffer for dissolution. When reconstituted, the volume is generally greater than 1.5 mL, which is difficult to administer especially for infants who exhibit infant reflux which could cause the vaccine to be thrown out. Of course this possibility is greater the greater the volume administered. Estimates indicate that current vaccine manufacturer have the ability to produce 50 million doses of rotavirus vaccine per year using a single dose model. If the demand for rotavirus vaccine is of 100 million doses or over, the single dose model would not be effective.

Accordingly, there is a need in the art for a new rotavirus vaccine with lower dose volume so a multi-dose vaccine could have smaller footprint resulting in cost savings along with less packing due to the heat stability to take care of cold chain issues. Another important advantage of developing such a heat-stable rotavirus vaccine is the assurance of proper vaccine potency during immunization campaigns.

SUMMARY OF THE INVENTION

The present invention overcomes the problems and disadvantages associated with current strategies and designs and provides new vaccines, compositions and methods for the treatment of infections.

One embodiment of the invention is directed to methods for the manufacture of bulk vaccine comprising: combining a buffering agent, a bulking agent, and an excipient containing at least arginine to a virus-containing composition forming a mixture, preferably wherein the virus titer of the mixture is $10^8$ FFU/ml or higher to reduce the total solids although heat stability remains is good even at lower titers; lyophilizing the mixture to form a lyophilized composition containing less than or equal to about 1.2% moisture or less; preferably 0.8% moisture or less, and milling the mixture to an approximate uniform particle size of 5 µm or less. Preferably the virus of the virus-containing composition comprises rotavirus and, also preferable, the rotavirus comprises multiple serotypes. Preferably the buffering agent comprises a mix of citrate and calcium carbonate, and maintains a pH of the mixture at about 7.0-8.0 which does not significantly change upon lyophilization. A significant change would be a change of about 1.0 unit, about 0.5 units, or about 0.1 units or less. Preferably the bulking agent comprises glucose, sucrose or both glucose and sucrose. Wherein the bulking agent is sucrose, preferably and the arginine to sucrose ratio is about 1:1.0 to 1:1.9. Arginine to sucrose ratios of 1:1.1, 1:1.2, 1:1.25, 1:1.3, 1:1.4, 1:1.5, 1:1.6, 1:1.7, 1:1.8, 1:1.9, 1:2, 1:2.1, 1:2.2, 1:2.3, 1:2.4, 1:2.5 and greater are preferred. Preferably the mixture comprises from approximately 2% to 6% arginine, and the mixture contains medium-chain triglyceride (MCT) oil. Preferably the bulk vaccine of the invention can be stored at room temperature for 2 years or higher at 50° C. for at least three months without any loss of efficacy; at 30° C. or higher for at least 24 months without significant loss of efficacy; and/or at higher to 40° C. for at least twelve months without significant loss of efficacy. A significant loss of efficacy would be a loss of about 10%, preferably a loss of about 5%, and more preferably a loss of about 1% or less. Preferably the method further comprises apportioning the mixture to individual doses containing virus at about $10^{5.9}$ FFU/mL and a volume of about 0.5 mL or less.

Another embodiment of the invention is directed to bulk vaccine manufactured according to the method disclosed herein.

Another embodiment of the invention is directed to bulk vaccine formulations comprised of a lyophilized rotavirus strain with excipients that provide thermo-stability at 30° C. for at least 2 years and at 50° C. for at least 3 months. Preferably the bulk vaccine formulation has at least a 90% uniform particle size of less than or equal to 5 µm no more than 10 micron for the balance, is homogenized with medium-chain triglyceride (MCT) oil, and/or contains citrate and calcium carbonate as buffering agents. Also preferably, the bulk vaccine contains individual doses of virus at about $10^{5.9}$ FFU/mL in a volume of about 0.5 mL or less.

Other embodiments and advantages of the invention are set forth in part in the description, which follows, and in part, may be obvious from this description, or may be learned from the practice of the invention.

DESCRIPTION OF THE DRAWINGS

FIG. 1. Examples of formulations screening method using 96-well plates. Each column (1-9) has one formulation type (A-I). Different excipient rations were tested in different columns.

FIG. 2. Accelerated stability studies at 40° C. for IVT-00 and IVT-01 formulations.

FIG. 3. Typical freeze drying cycle used for IVT-05 formulation that includes an annealing step before primary drying. Colors of the lines are described in the graph. Left and right Y axes describe the temperature and vacuum scales, respectively.

FIG. 4. Table of accelerated stability study for different batches of IVT-05 formulation at 40° C. showing that a reduction of moisture increases thermo-stability.

FIG. 5. Table of 12 month accelerated stability study at 30° C. for 116E Rotavirus in formulations IVT-05 and IVT-06 with 2% or 4% arginine.

FIG. 6. Table of 12 month accelerated stability study at 40° C. for 116E Rotavirus in formulations IVT-05 and IVT-06 with 2% or 4% arginine.

FIG. 7. Table of three month accelerated stability study at 50° C. for 116E Rotavirus in formulations IVT-05 and IVT-06 with 2% or 4% arginine.

FIG. 8. Graph showing stability data for vials containing 116E rotavirus lyophilized in IVT-06 formulation subjected to accelerated stability studies at 30° C. (blue diamonds) for 12 months, and 50° C. (red circles) for 3 months. The equations for the linear trend line of each temperature are shown.

FIG. 9. Table of three month accelerated stability study at 50° C. for Rotavirus in formulation IVT-06 with 2% and 4% arginine.

FIG. 10. Table showing the expected rotavirus titer in IVT-06 formulation after incubations at 30° C. and 50° C. for different periods of time based on the linear trend line equations obtained from the data presented in FIG. 8, and assume a starting viral titer of 5.6 $\log_{10}$ [FFU/mL].

FIG. 11. Expected titer over time for IVT-06 containing 2% or 4% arginine based on linear curves of trend line equations.

FIG. 12 Graph showing the average buffering capacity (n=3) of 0.2M citrate with different concentrations of calcium carbonate in 0.5 mL of IVT-06 final formulation analyzed by Baby Rossett-Rice assay (BRR). The final formulation is composed of micronized IVT-06 formulation and buffering components in MCT oil. The horizontal black line at pH 4.0 represents the lowest pH at which rotavirus is stable. The buffering mix is able to maintain the pH above 4.0 for 19-20 minutes (black arrow) with 80 mg of calcium carbonate.

DESCRIPTION OF THE INVENTION

Vaccines for the treatment and prevention of rotavirus infection are currently available. These conventional vaccines are orally administered and require cold storage before use. The formulations developed are prone to a substantial loss of virus titer due to thermal instability. Recent improvements in formulation development have resulted in liquid rotavirus vaccines that, when preserved at 2-8° C., remain fairly stable with minimal loss of titer. However, every potential failure of the cold-chain system, in other words failures in the hand off of cold vaccine from one facility to another, leads to a loss of potency in these vaccines. Incorporation of vaccine vial monitors (VVMs) has been useful to detect such events, but do not address the wastefulness of the current system.

Another concern with these conventional vaccines is the need for large volume per dose. At present, rotavirus vaccines are dose at volumes of 0.5 mL (ROTAVAC), 1.0 mL (ROTARIX and 2.0 mL (ROTATEQ). Larger volumes have been required to achieve the necessary amount of material per dose to generate a proper immune response when administered. However, a smaller volume per dose would necessarily be more efficient during manufacturing and allow for less complicated administration to patients. By way of comparison, the oral liquid Polio vaccine works well in the field with a few drops a dose (e.g., 5 drops or less, 3 drops or less, 2 drops or less).

Ideally, there is a need for a rotavirus vaccine that can be manufactured to be administered in a sufficiently low dose volume, and to be thermo-stable to address cold chain issues.

It was surprisingly discovered that a liquid, non-aqueous thermo-stable rotavirus vaccine formulation could be developed with reduced volume (e.g., 0.5 mL/dose and lower) predicted to maintain rotavirus stability for more than 24 months at 30° C., and six months at 50° C. The vaccine formulation of the invention improves the efficacy of universal rotavirus vaccine immunization program, thus reducing the burden associated with rotavirus infections in children. A multi-dose model will also reduce the final price of a vaccine dose by reducing costs associated with manpower and initial capital investments, and with less time needed for production.

Live viruses can be lyophilized using different excipients to impart heat stability. If this is done at titers of around $10^8$ FFU per ½ ml the resultant dried cake would have very high virus titer per unit of dried mass. When such a mass is formulated to a liquid batch, the volume of such a batch would be diluted almost 200 fold to reach a single vaccine dose of $10^{5.6}$ per 0.5 mL. The idea for this development is to use a non-aqueous vehicle to avoid any dissolution of the cake, while preserving the stability of the virus. Among the many vehicle possibilities, one medium chosen is a chain triglycerides oil (MCT) in part because MCT is used in infant formula for more than 50 years (one spoon has the equivalent of 1.8 mL of MCT oil). MCT is also under GRAS classification by the FDA, and has non-toxic effects in infants and adults. In addition, it was surprisingly discovered that a suspension of lyophilized and pulverized powder with oil remains in a lyophilized condition, in other words largely undissolved, the thus remains stable. The suspension including the buffer can be suspended in 0.5 mL, which is an easy to administer volume.

The oral rotavirus vaccine formulation comprises a lyophilized rotavirus strain with excipients expected to grant viral titer thermo-stability at 30° C. for at least 2 years, and 50° C. for 3 months. This solid lyophilized material is milled to a uniform particle size (<5 µm), mixed with a previously milled solid buffer (<5 µm), and finally suspended and homogenized in medium-chain triglyceride (MCT) oil, to create a final formulation. The final human dose is designed to have $10^{5.9}$ FFU/mL in a final volume of 0.5 mL.

To start the formulation development process, the naturally attenuated human rotavirus strain 116E (G9P[11]) was utilized as a model. This strain was originally isolated in New Deli, India in 1985 during an asymptomatic rotavirus infection outbreak in the newborn unit of the All India Institute of Medical Sciences (AIIMS). This is a reassortant strain containing a single bovine gene segment (VP4) in a human background (Glass at al., 2005), and has been successfully used by Bharat Biotech International for the recently approved ROTAVAC rotavirus vaccine in India (Bhandari et al., 2014a, b).

There were several desired characteristics in the lyophilized rotavirus formulation that were desired. Besides the long term titer thermo-stability profile, one desire was for a lyophilized material that ideally would have an elegant cake appearance with a low residual moisture profile, a short reconstitution/dissolution time in water with a final pH in the 7.0-8.0 range preferably with a pH of about 7.5 and preferable with a pH value that would not substantially change upon lyophilization. Preferably, lyophilizing the composition reduces the moisture content to about 5% moisture or less, preferably about 4% moisture or less, preferably about 3% moisture or less, preferably about 2% moisture or less, preferably about 1.2% moisture or less; preferably about 1% moisture or less, preferably about 0.8% moisture or less, or preferably about 0.5% moisture or less.

A matrix approach was used to test different excipients in different concentrations, with the goal of assessing their capabilities of imparting Rotavirus 116E stability in terms of titer and heat resistance over time. Various excipients were chosen according to current literature which can be classified as buffers, protecting agents, amino acids, salts, bulking agents, antioxidants and dispersants. Among the bulking and protectant agents, dextran and other lower molecular weight sugars such as sucrose, trehalose, and mannitol were utilized. These impart structure to a lyophilized cake, as well as provide protection to low concentrations of API in a formulation (Baheti et al, 2010). Among these agents non-reducing disaccharides also have the added benefit of forming an amorphous sugar glass upon drying, and have proven to be very effective in stabilizing and conferring long term stability to biologics such as enzymes, antibodies, and viruses (Carpenter, J. F, 2002; Liu et al., 2005; Johnson, R. E., et al., 2002). Different amino acids were also tested in the formulation (e.g., glycine, a known bulking agent, glutamate, histidine, and arginine). The former typically crystallize to a substantial degree during lyophilization (Pikal, 1994; Carpenter and Chang, 1996), and the latter was tested because of its anti-aggregation properties during lyophilization of proteins (Stärtzel, et al., 2015). Buffers such as Tris, Hepes, phosphates and histidine were also tested to maintain a constant pH before, during, and after the freeze-drying process.

A factorial designed analysis was implemented using 96-well plates with tailor-made aluminum plate adaptors to homogeneously distribute the heat of each well to these rotavirus-containing formulations during the lyophilization cycle. A conservative freeze drying cycle was stablished to guarantee the stability of these formulations.

Evaluation and selection of the best formulations in this factorially-designed preliminary screening was based on the cake appearance, as well as the rotavirus titer data for each lyophilized formulation combination, using an in-house focus fluorescent assay (FFU/mL). As controls, these titers were compared to their corresponding liquid formulations (non-lyophilized) to evaluate the relative influence of excipients on titer loss during the freeze drying process.

JMP10.0 software (SAS Cary, USA) was used to analyze the effect of the different excipient combinations on virus stability for each formulation. All statistical analysis was performed using a confidence level of 95% (P=0.05).

FIG. 1 shows a typical 96-well plate with different formulations during the selection process. Individual formulations were arranged by columns; and shows that some formulations have collapsed cakes (e.g., compare columns 1 and 2); while others have perfectly homogeneous cakes (e.g., compare columns 3, 4, 7, and 8). This data mining process allows for selection of the top four formulation candidates and evaluation individually in glass vials. Formulations were further optimized and a lead lyophilization formulation selected.

From the theoretical freeze drying processing perspective, a lyophilized rotavirus formulation was obtained that had the following characteristics. First, excipients capable of generating a well-structured, porous, and stable cake were combined. Second, a cake that could have a fast reconstitution time when mixed with reflux or gastric liquid in the stomach and dissolved in water, and leave no particles in suspension. Third, a formulation with a mix of excipients that would impinge the cake with the highest glass transition temperature (Tg) possible. The glass transition temperature, often called Tg, is an important property when considering polymers for a particular end-use. Glass transition temperature is the temperature, below which the physical properties of plastics change to those of a glassy or crystalline state. This is a crucial point for the development of this formulation because there is ample evidence that, a higher glass transition temperature Tg leads to a greater stability at higher temperatures, over time (Bronshtein, V., 2001; Carpenter, J. F., 2002). Thus, vaccines with a Tg of 37° C. or higher are suitable for transport at room temperatures (e.g., 20-35° C.), but not much greater. Fourth, the excipients in the formulation should contribute a reasonable quantity of solids after freeze drying, so that the final quantity of dried particles in the oil suspension is still flowable. Lastly, a freeze drying cycle was that would be amenable for the lyophilized formulation to have the lowest residual moisture possible, since low moisture is necessary for long term stability and help increase the glass transition temperature (Carpenter, J. F., 2002). The Tg of the immunogenic compositions of this disclosure are preferably 37° C. or greater, 40° C. or greater, 45° C. or greater, 50° C. or greater, 55° C. or greater, 60° C. or greater, 65° C. or greater, 70° C. or greater, 75° C. or greater, 80° C. or greater, 85° C. or greater, or 90° C. or greater.

Among the four formulations candidates selected from the original screening, two, IVT-00 and IVT01, were chosen for their good cakes and low titer loss during the lyophilization process ($10^{\leq 0.3}$ FFU/mL). Both formulations had 7.5% sucrose as a cryo-protectant, phosphates as buffer system, a low amount of glutamate for virus stabilization, and MEM or DMEM growth media, which were contributed from the 116E Rotavirus stock.

A long, conservative lyophilization cycle (~100 hours) was used to obtain the lowest moisture as possible for these formulations. This involved a long (70 hours) primary drying at temperatures of minus 40° C. and minus 35° C., followed by a 10-hour ramp to the secondary drying temperature of 25° C., to finally hold at this temperature for another 15 hours.

Formulations were freeze dried in vials with the above cycle and subjected to accelerate stability studies at 40° C. Results are shown in FIG. 2. IVT-00 formulation was capable of maintaining rotavirus stability for two weeks at this temperature with a loss of $10^{0.2}$ [FFU/mL], but the cake changed color, collapsed, and shrunk after two weeks, mostly due to its high residual moisture (2.4%). Further titer determinations for this formulation were stopped.

The IVT-01 formulation had a lower moisture content (1.74%) than IVT-00, and its cake was stable, but was unable to maintain the stability of the 116E rotavirus with titer losses of 0.95 $\log_{10}$ and $10^{1.41}$ [FFU/mL] at 1 and 2 months of incubation at 40° C., respectively.

In attempts to increase the stabilities of these formulations after lyophilization, glass-transition temperatures (Tg) were measured using DSC calorimetry to increase the secondary drying temperature of the lyophilization cycle and thus reduce their residual moisture. Results showed that IVT-00 and IVT-01 formulations have a Tg of 49.3° C. and 53.8° C., respectively. Temperatures of the secondary drying were increased during the lyophilization cycle from 25° C. to 30° C., and 35° C., and the formulations were subjected to new lyophilization cycles. Although their final moisture content was lowered, the stability titer of the rotavirus at 40° C. did not improve, suggesting that the excipients in these formulations were not able to confer thermo-stability. Further analysis of these two formulations was stopped.

Using a similar approach, the thermo-stability of the two remaining formulations selected from original screenings, IVT05, and IVT06 were analyzed. The excipients present in the IVT-05 formulation included MEM growth media, sucrose, glycine, and glutamate. Both sucrose and glycine are common bulking agents, which imparted a good structure to the IVT-05 cake after lyophilization using the conservative freeze drying cycle described above. The structure and mechanical properties of the cake was improved by modifying the freeze drying cycle for IVT-05. Other agents that may be utilized include lower molecular weight saccharides and polysaccharides and sugar alcohols (e.g., fructose, glucose, galactose, trehalose, xylose, lactose, maltose, mannitol, sorbitol, glycerol).

There are two important aspects during the freeze drying process that when balanced, form a good cake. The first is an excipient that forms an amorphous phase, capable of protecting proteins or viruses during freeze drying, and confer thermo-stability (Johnson et al., 2002). Disaccharides, like sucrose in the IVT-05 formulation, is known to form an amorphous sugar glass and has been used as an effective stabilizer of liposomes and proteins during lyophilization (Colaco et al., 1992; Crowe et al., 1993; Crowe 1993b; Leslie et al., 1995). The second aspect is the presence of a component that promotes structural support for the cake, usually given by an excipient that has the tendency to crystalize during lyophilization. Glycine, in particular, is known to crystalize during lyophilization (Pikal et al., 1994; Akers, et al., 1995; Carpenter and Chang, 1996), and usually includes a controlled freezing step before—primary drying to maximize its crystalline state (Lu et al., 2004; Searles et al., 2001). This also reduces the resistance to sublimation of water molecules in the formulation by creating a porous cake, accelerating the primary drying and therefore shortening the freeze drying cycle (Lu et al., 2004; Searles et al., 2001). Buffers that may be used for lyophilization include, for example, Tris-HCl, HEPES, phosphate buffers and histidine buffers.

Figure 3:
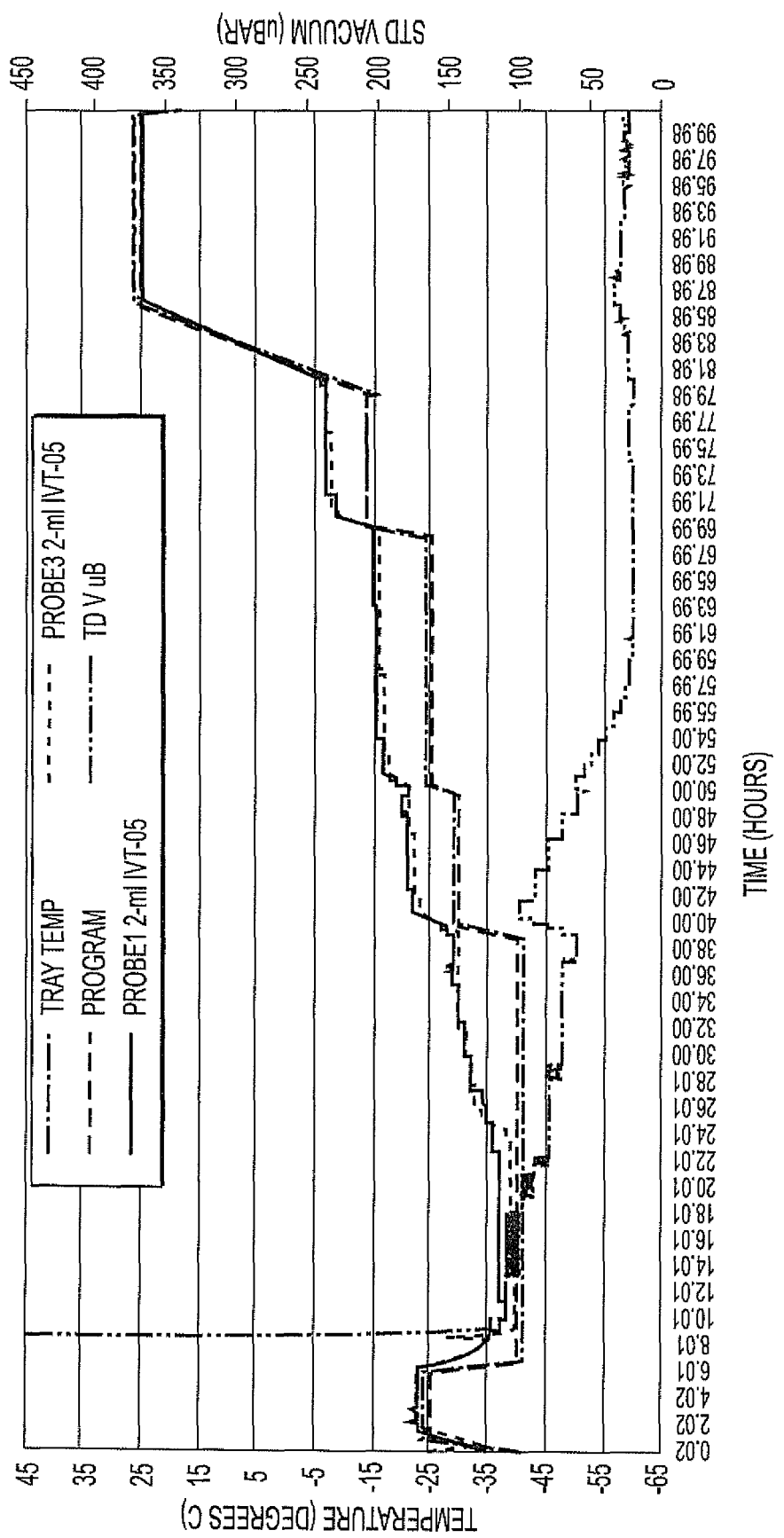

The successful lyophilization of proteins involves balancing two competing aspects: a well formed cake that does not collapse during primary drying, and the existence of an amorphous phase where molecules of excipient are free to interact with the protein. Based on this information, the original freeze drying cycle was modified to evaluate the thermo-stability of the IVT-05 formulation at 40° C. FIG. 3 shows the new freeze drying cycle. After freezing the vials with controlled freezing to minus 40° C. Based on the experience gained in previous freeze drying cycles, the primary drying step was modified from a linear to a gradual increase of temperatures and steps during 79 hours of the cycle. Secondary drying was performed at 25° C. for 15 hours (FIG. 3).

One hundred 5.0-mL glass vials were prepared, each filled with 2.0 mL of IVT-05 formulation containing 116E rotavirus, and inserted temperature probes in two of them to follow their thermal properties during lyophilization (purple and broken red line, FIG. 3). They both follow a similar pattern, having a slight increase in temperature during first 24 hours of the cycle, when compared to the shelf temperature (thick red line). This indicates that the excipients are bestowing the IVT-05 formulation with an effective sublimation rate. The vacuum (green line, FIG. 3), which was set at 25 μbars, reached this value at approximately 60 hours into the freeze-drying cycle, indicating that the end of the primary drying step is achieved at that time.

At the end of the cycle, vacuum was broken with ultra-pure nitrogen gas rather than atmospheric air to avoid introducing moisture back in the system. The vials were pneumatically stoppered inside the freeze drying chamber, and immediately clamp-sealed with aluminum caps. The lyophilized cake obtained can be described as elegant, light, porous, and well-structured. Dissolution of the cake with 2 mL of WFI took less than 35 seconds, and did not have any particulates present.

Some of the vials of this lyophilized IVT-05 formulation (Batch 5.1) were incubated in chambers at 30° C. and 40° C. to subject the virus to accelerated stability studies over time. Another group of vials were stored in the minus 80° C. freezer, and used as controls (time zero; t=0). For comparisons, a second lyophilization batch (IVT-05 Batch 5.2) was prepared using the same protocol described above.

The monthly titer of the formulations was determined using a focus fluorescent assay (FFU/mL). The average variability of this assay after 21 independent titer determinations of the 116E rotavirus stock was +/−$10^{3.3}$ [FFU/mL]. This means that a titer loss within this value should be considered acceptable as no titer loss.

The results of the stability study (viral titer; [FFU/mL]) at 40° C. for both batches are summarized in FIG. 4. The data shows that IVT-05 batches 5.1 and 5.2 were capable of imparting thermo-stability at 40° C. for only one month, with titer losses of −0.13 $\log_{10}$ and −0.28 $\log_{10}$ [FFU/mL], respectively. Further incubations at 40° C. resulted in increasing higher titer loss, reaching a value of about −1.5 $\log_{10}$ after 6 months of incubation. Although the stability was lower than expected, IVT-05 batch 5.2 was twice as stable as batch 1 after 4 months (−0.48 vs −09 $\log_{10}$ loss).

Residual moisture determinations (FIG. 4) for both batches show that they have higher than expected moisture, with batch 5.2, having about 0.2% less than batch 5.1. Knowing that increased moisture affects the long-term stability of a formulation, these results indicate that reducing the final moisture content in the IVT-05 formulation would increase overall stability. To this effect, instead of modifying the primary drying step of the cycle described (FIG. 3), the secondary drying temperature step was increased from the current 25° C.

Before selecting the temperatures to be tested, the glass transition temperature (Tg) of IVT-05 formulation was measured using differential scanning calorimetry (DSC). This technique measures the temperature at which the solid IVT-05 cake transitions to a liquid form, and is important to set secondary drying temperatures during lyophilization. As a rule of thumb, the higher the Tg, the higher the secondary drying temperature permissiveness.

DSC results showed that IVT-05 has a Tg of 59.13° C. This is about 10° C. and 5° C. higher than the previous IVT-00 (Tg=49.39° C.) and IVT-01 (Tg=53.82° C.) formulations, and shows that an increase of 10° C. in Tg would increase the thermostability.

Two new IVT-05 batches were produced which were exposed to either 35° C. (Batch 6B), or 40° C. (batch 6C) during their secondary drying step. Their thermo-stability and final moisture content results are also presented in FIG. 4.

By reducing their moisture contents, the respective 116E rotavirus thermo-stability at 40° C. increased from 1 month (Batches 1 and 2), to 4 months (Batch 6B), and 6 months (Batch 6C), respectively. These results confirm the notion that reduced residual moisture increases long term stability. (Carpenter, J. F., 2002).

One of the formulation identified in the original screening was named IVT-06. This formulation is similar to IVT-05 with two exceptions: it contains the amino acid arginine rather than glycine, and also contains a small amount of Hepes as a buffering agent to stabilize the pH before, during and after freeze-drying. The same lyophilization cycle described above utilized for IVT-05 Batch 6C formulation (FIG. 3, and FIG. 4) was used for lyophilization of IVT-06, and IVT-06 formulation containing 116E rotavirus with 1%, 2% or 4% w/v of arginine was then tested. A new batch of IVT-05 was also formulated and used as a control for comparative purposes. Additional amino acids that are utilized in formulations of the disclose include amino acids containing an alpha amino group and an alpha carboxylic acid group, Gly, Glu, Gln, His, Ile, Leu, Lys, Met, Phe, Thr, Trp, Val and combinations thereof.

After lyophilization, all four formulations were measured and compared for their moisture content, dissolution time, and pH stability. Final moisture content determination by Karl Fisher analysis (n=3 per sample) revealed that all three IVT-06 formulations contained much less residual moisture compared to the IVT-05 formulation (0.94%). In this regard, an inverse effect was observed: increasing concentrations of arginine in the IVT-06 formulations resulted in reduced final moisture, with IVT-06 plus 4% Arginine having the lowest moisture (0.43%). This indicates that the IVT-06 formulation has the potential to have an improved rotavirus stability profile compared to IVT-05, as reduced moisture increases the Tg value and stability of a lyophilized cake (Carpenter, J. F., 2002). Measurements of the dissolution time with WFI for all three IVT-06 formulation cakes also showed an improvement over IVT-05 (35 second), with an average of 15 seconds for all three arginine-containing formulations.

The pH before and after lyophilization for IVT-05 was measured and all three IVT-06 formulations as an indicator of pH stability during the freeze-drying process (n=3 per sample). The liquid IVT-05 formulation was observed to have a pH of 6.9-7.0, which shifted by an average of 0.5 pH units to the basic pH scale after lyophilization (suspension pH ~7.5). In contrast, the presence of Hepes buffer in all three IVT-06 formulations, tested under the same conditions, showed only a slight shift of 0.1 pH unit (pH 7.19 to 7.29). These results indicate that the presence of Hepes buffer in all three IVT-06 formulations imparts better pH stabilization. To test if this could improve pH stability in IVT-05, the same amount of Hepes buffer present in IVT-06 was added, and analyzed under similar conditions described above. Similar to IVT-06, the pH shift was reduced to 0.1 pH units in IVT-05, thus confirming the beneficial effect of Hepes addition.

Overall, the IVT-06 formulation, and in particular the one containing 4% arginine, show an improvement over IVT-05 in lowering the moisture content and keeping the pH constant. This would indicate a better Tg value and so better thermostability. To confirm this observation, the lyophilized 116E rotavirus in IVT-05, and two IVT-06 formulations with 2.0% and 4.0% arginine were subjected to accelerated stability studies at 30° C. and 40° C. for 24 months, and at 50° C. for 3 months. Results for twelve-month stability data at 30° C. for this ongoing study are summarized in FIG. 5. Considering the intrinsic error in the focus fluorescent viral titer assay of +/−0.33 $\log_{10}$ [FFU/mL], all three formulations showed no loss of viral titers as the values obtained were smaller than the assay error and these showed the same over the 12-month study period. This demonstrates that all three formulations are capable of maintaining the 116E rotavirus strain stable at 30° C. Based on this data, the IVT-06 containing 4% arginine is the best formulation so far, as it has the least titer loss (−0.13 [FFU/mL]) after 12 months. This observation is confirmed with accelerated stability studies at 40° C. for 12 months, which are summarized in FIG. 6. At this temperature, only the IVT-06 with 4% arginine formulation is still capable of imparting thermo-stability to rotavirus 116E, with a calculated titer loss of only −0.08[FFU/mL]. In comparison, freeze dried rotavirus in IVT-05 formulation showed stability for 8 months. The latter has two months of longer stability than what had been observed in the previous IVT-05 batches shown in FIG. 4. Since those studies were stopped at 6 months, if they were continued—in particular with Batch 6C, stability observed would be similar to 8 months.

Figure 9:
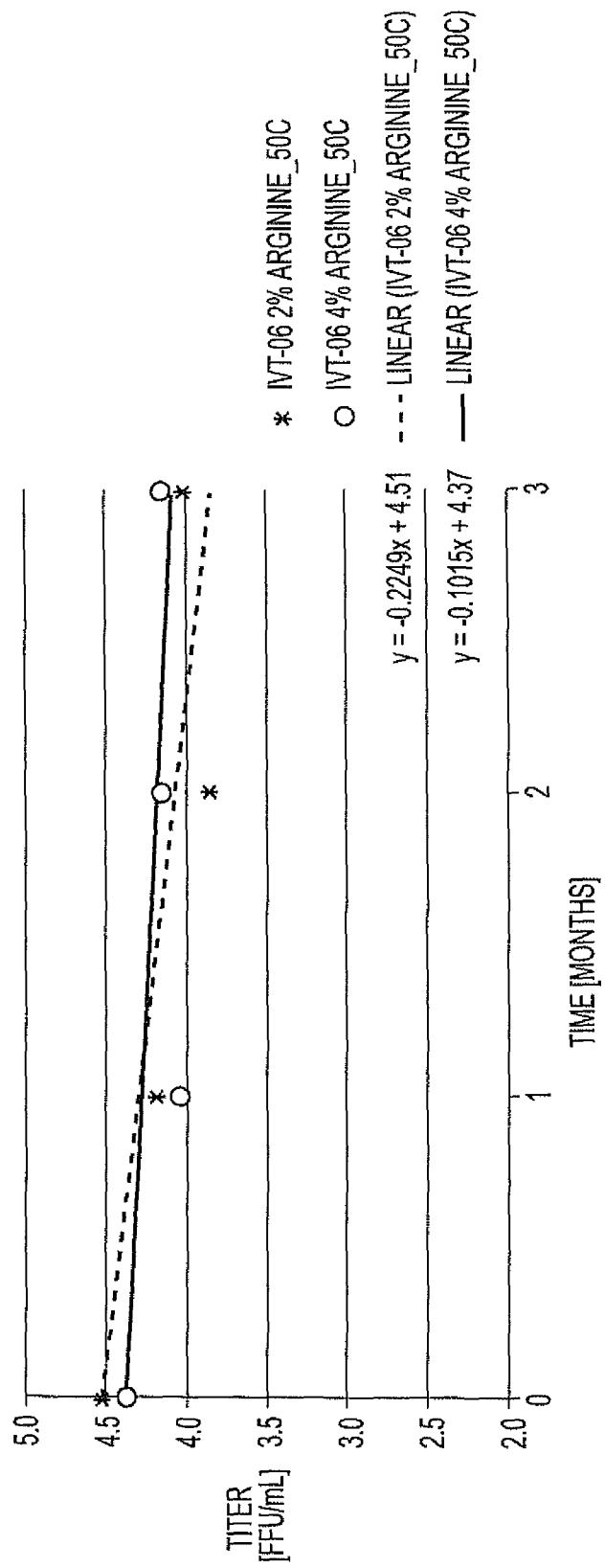
Figure 12:
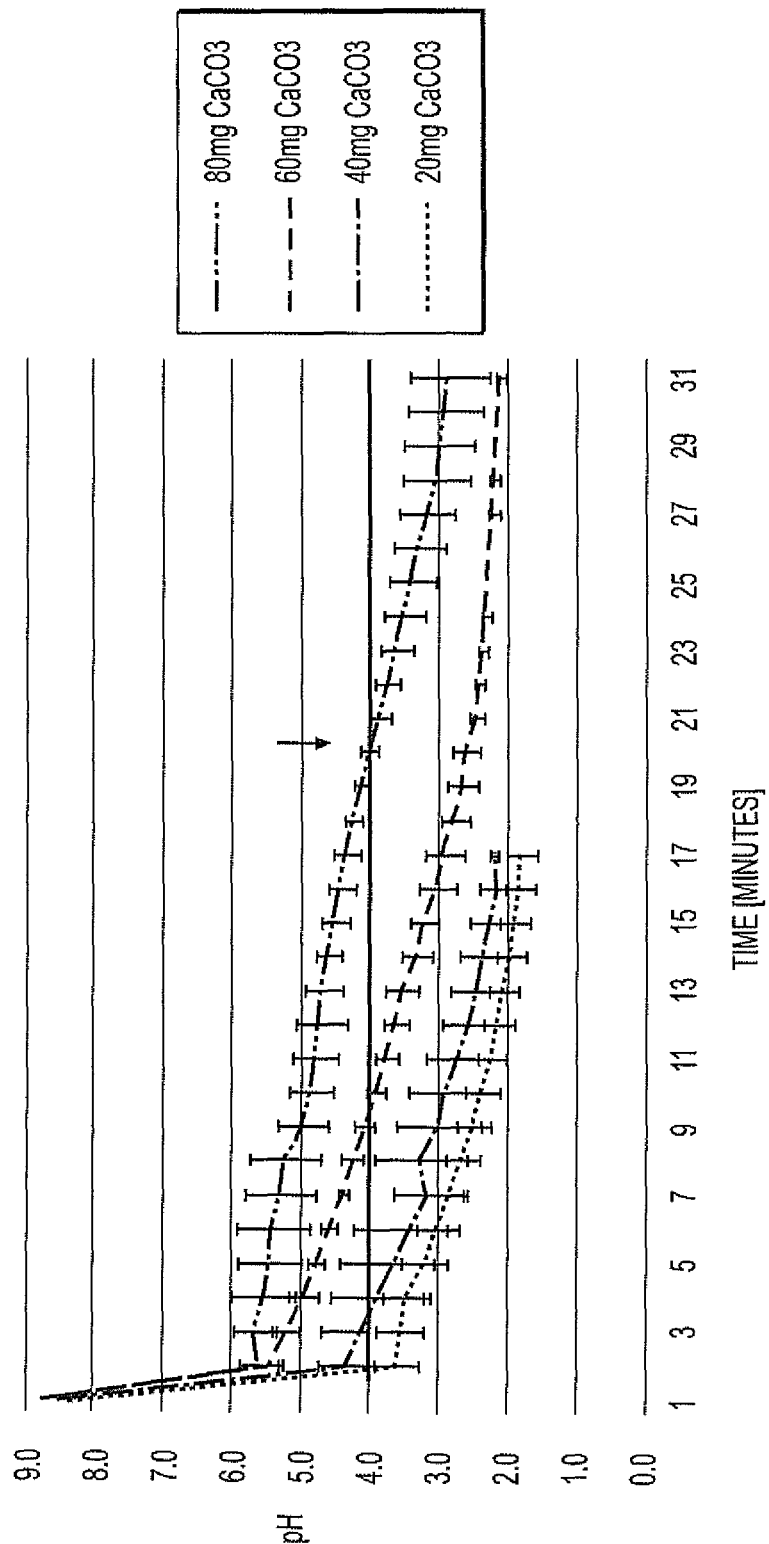

Accelerated stability studies of these three formulations were also exposed for 3 months at 50° C. (see FIG. 9). A 3-month study was performed showing that only IVT-06 of these formulations was capable of stabilizing rotavirus at such a high temperature for a period longer than 3 months. The results are presented in FIG. 7. The data shows that the differences in stability observed at 40° C. for all three formulations are similar. Only the IVT-06 formulation containing 4% arginine continues to impart thermo-stability to rotavirus 116E at 50° C. after 3 months with no loss (only −0.22 [FFU/ml] $\log_{10}$ loss, which could be error of testing), while IVT-05 stabilized for 2 months, and IVT-06 with 2% arginine only for 3 months.

The three formulations here impart rotavirus thermo-stability for at least 12 months at 30° C. Only IVT-06 with 4% arginine showed stabilizing live rotavirus at higher temperatures: at least 12 months at 40° C. and more than 3 months at 50° C. This data also defines IVT-06 with 4% arginine as a lead-formulation, which is termed simply as IVT-06.

Figure 8:
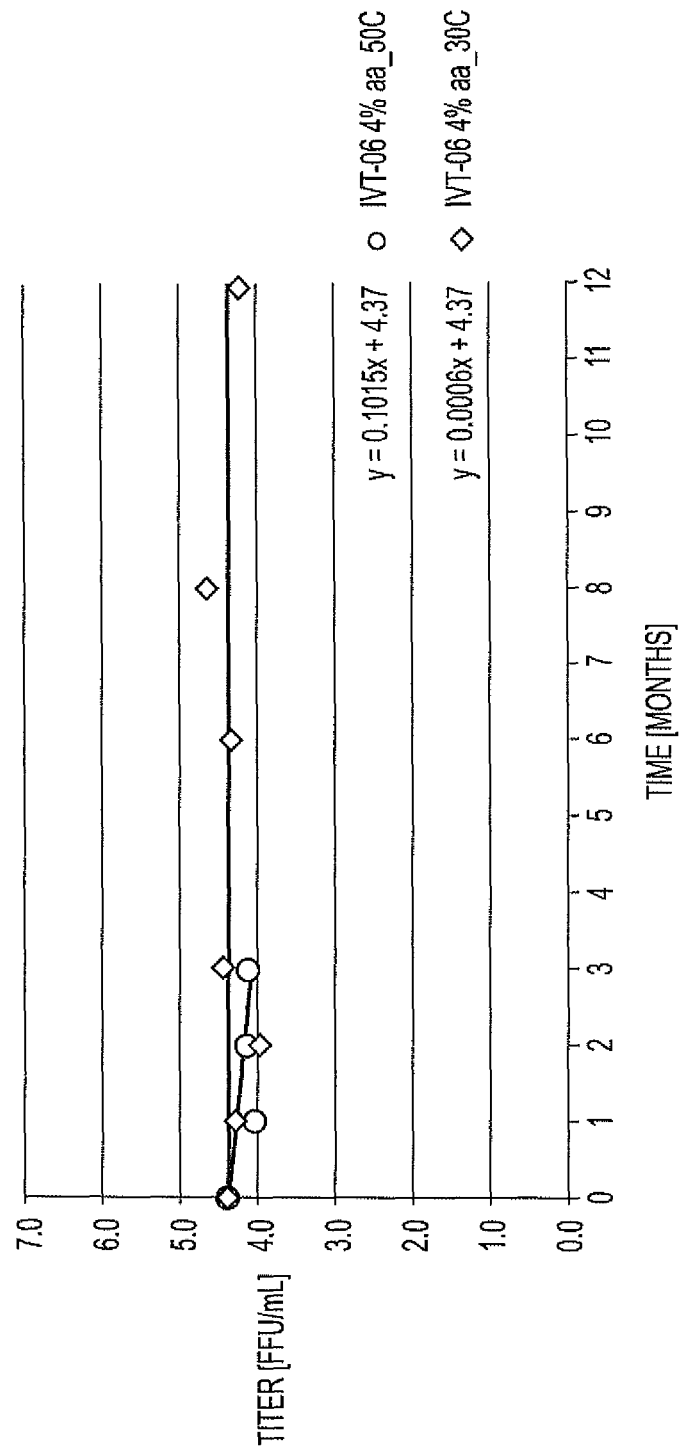

A summary graph showing the stability of 116E rotavirus in IVT-06 at 30° C. and 50° C. is shown in FIG. 8. The linear trend line for the 30° C. (blue line) and 50° C. (red line) titer data were calculated, and their equations are presented within the graph. In each linear equation, the Y factor represents the final titer, the negative factor is the slope of the linear trend representing the titer loss over the time X (in months). The 4.37 factor is the original titer at time zero. The trend-line for IVT-06 formulation incubated at 50° C. (red line) has a bigger negative slope (−0.1052) compared to the 30° C. incubation (blue line; −0.0006 slope).

According to WHO guidelines for the production of live attenuated oral rotavirus vaccines (WHO TRS No 941, annex 3, 2007), a vaccine should contain an equivalent of at least 5.0 $\log_{10}$ titer [FFU/mL] after the recommended two-year shelf life storage at 2-8° C. Rotavirus vaccine manufacturers usually give themselves an allowance of 0.6 log loss in titer for these two-year incubation, accounting to a stating titer at time zero of 5.6 $\log_{10}$ [FFU/mL] per human dose.

Using the trend-line equations described above (see FIGS. 4-7), FIG. 8 shows the expect titer after incubation (in months) at either 30° C. or 50° C. for IVT-06 formulation, starting with a rotavirus concentration of 5.6 $\log_{10}$ [FFU/mL] at time zero. The calculations under these conditions shows that the IVT-06 formulation is expected to be stable for 24 months at 30° C. with minimal titer loss, and at least 6-9 months stability at 50° C. before the rotavirus titer loss get to the minimum WHO requirement of 5.0 $\log_{10}$ [FFU/mL]. Based on accelerated stability titer data and the trend-line presented in FIGS. 10 and 11, an oral rotavirus vaccine produced in IVT-06 lyophilized formulation could be stored without the need of refrigeration, in a cool-dry place, with almost no titer loss over a period of two years. On developing the lead thermo-stable IVT-06 lyophilized rotavirus formulation, a final formulation was designed for the vaccine, with the main objective of preserving the rotavirus stability under lyophilized conditions. The new vaccine formulation includes the micronization of the lyophilized rotavirus material and buffering agents (as below) in medium chain triglycerides (MCT) oil to create a homogenized oil suspension. Micronization sizes used are based on organoleptic properties. The micronization diameter chosen avoids infants (e.g., 3-6 months) choking due to ingestion of suspension material.

Since rotavirus vaccines are orally administered to infants at an age where they are still on a liquid diet (e.g., breast-milk or milk formula), it is important to consider the micronization process and the average particle size in the final formulation suspension so that it would remain acceptable because of its organoleptic properties.

Food texture, including the sensory properties of particle size, plays an important role in its acceptance at an early age (Lukasewycz and Mennella, 2012). Each crystalline material has a critical detection size threshold, where the mouth detects coarseness. This depends on the properties of the crystal, namely, how rapidly they dissolve in the mouth. Lactose crystals, for example, are detected by adults at 15 micro meters [μm] size or larger (Hartel, 2008). Infants, on the other hand, detect coarseness in crystal particles size above 5 μm in size.

Both the IVT-06 lyophilized rotavirus formulation and buffering agents were micronized to particle sizes of 5 μm or less by jet milling (Parrot, 1974). Reduction is achieved by colliding particles in a toroidal chamber under a high flow of gas. An added benefit of using this system is that it does not generate heat during the micronization process, making it useful for handling biological samples like proteins or viruses (Naik and Chaudhuri, 2015). To preserve the low moisture content of the lyophilized IVT-06 formulation during the milling process, the jet mill was utilized inside a glove box and the micronization was done using inert nitrogen gas.

Both the mill's nozzle pressure, and the rate at which the sample to be micronized is fed into this system are important to control the extent of the particle size reduction. After milling both components, the respective amounts of solids present in the final formulation of the vaccine were mixed under nitrogen gas inside the glove box, considering that the final volume of one human dose is 0.5 mL. To these solids mix were added the respective amount of medium-chain triglycerides (MCT), and homogenized it to create the final suspension formulation of the vaccine.

MCT was picked as a vehicle for the final vaccine suspension formulation because it has very low moisture content (ppm levels), and therefore helps to preserve the Tg of the lyophilized virus with low moisture conditions. MCT oil is a non-aqueous liquid that prevents dissolution of micronized thermostable Rotavirus vaccine (e.g., IVT-06). Two micronized solid buffers can be used (e.g., calcium carbonate and trisodium citrate anhydrous) to prevent stomach acid from killing an attenuated virus. The particle size of these added buffer particles is also 5 microns or less. As explained before the chemically reacted MCT oil-with other chemicals to form liposomes as a vehicle for delivery of the formulation is not possible. So, it is not an existing art equivalent to our idea of using MCT oil. In addition, MCT has been used therapeutically since the 1950s, and increasing number of food and nutrition applications such as the fat component in infant milk formulas, adult dietary supplements, baked goods, beverages, chewing gum, confections and frostings. MCTs are also found naturally in milk-fat, including human breast milk (5-15%). MCTs have typically been used in diets for children at 15-30 gm/day, and 40-100 gm/day in adults, covering up to 40% of the daily energy requirements without having any toxicological effects (Bach, et al., 1996). MCT oil was therefore used as a vehicle as a safe alternative for the development of vaccine formulations.

Small batch experiments indicate that live rotavirus is stable in such a formulation at time zero, and the virus was extracted from milled IVT-06 formulation in MCT with approximately 100% recovery.

116E Rotavirus batches can be grown in WHO-certified Vero cells and a preferred titer is $\geq 10^7$ titer. To eliminate the dependency of primary antibodies for the detection of infective rotavirus particle, a quantitative reverse-transcriptase polymerase chain reaction assay was developed (qRT-PCR) for titer determination. This assay is comparable to the WHO-approved potency assay (Ranheim, et al., 2006).

Rotaviruses are known to be acid-labile, and are rapidly inactivated in the stomach gastric acid with a half-life of seconds at pH 2.0, about 12 minutes at pH 3.0, and stable at pH4.0 (Weiss, and Clark., 1985). Since rotavirus vaccines are orally administered, to increase their effectiveness, they require a buffering system before or during vaccination to counteract their inactivation in an infant stomach acidic environment (pH 1.8-2.0). Multiple assays have been developed to study the effectiveness of antacids in an acidic environment (Washington, N., 1991). Among them, the baby Rossett-Rice (BRR) assay is regarded as the best in vitro assay that closely mimics the stomach and its acid secretion in a 6-month old infant (Washington, N., 1991; Rossett and Rice, 1954; Vande Velve, V., 2012).

Buffers used in liquid rotavirus vaccine formulations found in the current market use a combination of di or tri-carboxylic acid salts, most commonly citrate or adipate, sometimes complemented with phosphates. In particular, ROTATEQ (Merck) uses a combination of sodium citrate and sodium phosphate buffers with some sodium hydroxide in their vaccine formulation. The recently approved monovalent vaccine from Bharat Biotech in India uses a combination of sodium citrate, phosphates, and bicarbonate, while ROTARIX (Glaxo SmithKline) use sodium adipate as its sole buffering system in the European market.

Inorganic salts present in the GRAS list (generally recognized as safe), a register of chemicals selected by the United State Food and Drug Administration (US-FDA), were tested for buffering capacity in the BRR assay using 0.5 mL volume of IVT-06 final formulation (milled lyophilized IVT-06 and buffering salts, suspended in MCT described herein. The objective being to measure the time at which these buffer systems are able to maintain the pH above pH 4.0, since rotaviruses do not lose their infectivity potential at this pH.

Initially the buffering system is composed of sodium citrate and sodium adipate mix which had a buffering capacity of 15 minutes above pH 4.0 for a 0.5 ml vaccine formulation of milled IVT-05 or IVT-06 in MCT oil. Incubation of either formulation at temperatures above 30° C. for more than 3 weeks resulted in an increased gelification of the milled material in MCT oil over time. This led to a permanent separation of the solids from MCT with their eventual hardening over time. Gelification was much more pronounced with the milled IVT-05 formulation compared to IVT-06. Mass-spectroscopy analysis of these temperature-exposed samples revealed the presence of N-acyl bonded adducts between glycine, present in the IVT-05 formulation, and C8 (caprylic) or C10 (capric) fatty acids. These two fats are the major components (66% of caprylic and 32% of capric) in MCT.

Low amounts of N-acyl amino acids are commonly used as gelling agent for nonpolar liquids (e.g., MCT) in the absence of water (Saito et al., 1976) were most advantageous. This indicates that the potential culprit for the gelification process in IVT-05 is due to the formation of these adducts. It was observed that the replacement of the amino acid glycine in IVT-05 for arginine in the IVT-06 formulation avert gelling over time at temperatures around 30° C. to a great degree. Mass spectroscopy also identified the formation of monoesters between sucrose present in the formulation, and the C8 or C10 fatty acids present in MCT oil. Sucrose-esters are natural, non-toxic, biodegradable nonionic surfactants commonly used in the food, cosmetic and pharmaceutical industry (Polat and Linhardt, 2001; Moran M C, et al., 2004). As such, they have been regarded as safe by the US-FDA, WHO and the EFSA regulatory authorities.

The original buffering component—sodium adipate—formed an adduct with two C8 fatty acids molecules (dioctanoyl monoadipoyl glyceride). Although its contribution to the gelification of the IVT-05 formulation in MCT is not clear, it is an alternative buffer in some formulations. Two-year old IVT-05 formulations in MCT, kept at room temperature, which contained alternative buffering systems, were analyzed. Multiple bottles of IVT-05 formulation in MCT whose milled components were distinctly in suspension (e.g., not hardened or gelified). These bottles contain calcium carbonate, rather than sodium adipate, and sodium citrate as buffering components.

FIG. 12 summarizes the results of BRR assays assessing the buffering capacity of a milled (<5 μm) mix containing a constant concentration of 0.2M sodium citrate with increasing concentrations of calcium carbonate. These buffer mixes were tested in a final volume of 0.5 mL containing milled IVT-06 in MCT. The graph shows a direct correlation between increasing concentrations of calcium carbonate and buffering capacity in the 0.5 mL formulation, and defines 80 mg as the best concentration of calcium carbonate in the buffering mix. Under these conditions, the graph shows that at time zero, immediately after the addition of the 0.5 mL formulation to the BRR assay, the initial pH is 8.7. After the immediate addition of 4 mL of 0.1 N hydrochloric acid (pH 1.8), which models the gastric acid content in an infant's empty stomach, the buffering mix in the formulation is capable of neutralizing the acidity to pH 5.6 (see 1-minute time in the graph). Thereafter despite the constant pumping of 0.1N hydrochloric acid (0.5 mL/min) to the assay, representing the stimulation of acid secretion in the infant's stomach, calcium carbonate added is able to maintain the pH above 4.0 for 19-20 minutes (black arrow). As a reference point, the buffer system present in the ROTARIX (GSK) vaccine used in the European market is able to maintain the pH above 4.0 for 12 minutes under similar BRR test conditions (Vande Velde., 2012). This indicates that this new buffering system is better than those used in currently approved rotavirus vaccines in the market, and identifies the 0.2M citrate/80 mg calcium carbonate mix as a better buffering system for vaccine.

There are a few advantages of having calcium carbonate rather than adipate in this new lead buffering system: i) longer buffering capacity than the previous system; ii) lack of gelling or hardening of the formulation at 30° C.; iii) highly insoluble in water, but dissolves easily under acidic condition (i. e: infant stomach); and iv) remaining as an undissolved solid in MCT without affecting the pH of the formulation and the moisture content, to name a few.

To clearly assess the gelling time if any, and formation of adduct over time in the IVT-06 formulation with this buffering system in MCT, bottles of this formulation were placed at 4° C., 30° C., 40° C. and 50° C. for observation and mass-spectroscopy analysis.

To improve the prevention of diarrheal diseases produced by rotavirus infection in infants of low and medium-income countries, it is important to have a second generation of a live attenuated oral rotavirus vaccine that is potent, low volume, cost-effective, thermo-stable at ambient temperature, and does not require reconstitution or external buffering systems.

A new liquid thermo-stable rotavirus vaccine formulation with reduced volume (0.5 mL/dose) of the invention is predicted to maintain rotavirus stability at 30° C. for more than two years and at 50° C. for six months. The vaccine of the invention is composed of a micronized lyophilized rotavirus vaccine formulation with buffering components of a particle size of less than 5 μm, and are suspended in MCT. Due to rapid solubility this suspension does not require reconstitution. Current rotavirus vaccines in the market: ROTATEQ (Merck; Vesikari, et al., 2006), ROTARIX (GSK; Vesikari et al., 2007), and ROTAVAC (Bharat Biotech; Bhandari et al., 2014a, b), are based in an aqueous formulation with volumes of 1.5-2.0 mL per human dose that are required to be stored at 2-8° C. or lower to maintain rotavirus stability. In contrast, the formulation of the invention vaccine is unique in many respects, and present many improvements and cost-reductions compared to the ones currently available.

With enhanced thermo-stability, the vaccine formulation of the invention allows it to be removed from cold chain storage, eliminating cost associated with low temperature storage, use of cold-packs during transportation, and personnel associated with its logistic planning. Thermo-stability also has the potential to reduce cost by stocking vaccines in room temperature facilities in the supply chain, especially during the course of vaccination campaigns. This has the added benefit of increasing the vaccination coverage to more remote rural areas in different countries.

Vaccine stakeholders from different counties agree that just by increasing thermo-stability in vaccines could drastically improve their vaccination programs (Kristensen, 2016), and improves the vaccination coverage by increasing the probability of immunizing with a fully efficacious rotavirus vaccine dose. The additional benefit of this increased efficacy is the reduction of the overall vaccination campaign cost over time. As used herein efficacy can be measured as a titer and no significant loss of efficacy may mean less than 5%, preferably less than 4%, preferably less than 3%, preferably less than 2%, and preferably less than 1%.

Reducing the final volume of this rotavirus vaccine to a 0.5 mL per dose easily allows for packaging it in a small multi-dose form, which allows for benefits at least in the form of cost reductions for thermo-stability which are enhanced under a multi-dose modality. A low volume multi-dose vaccine presentation also makes the vaccination process faster and more manageable than vaccinating with the current 1.5 to 2 mL doses currently available in the market. From the manufacturing perspective, a ready to use multi-dose vaccine formulation can also boost the capacity output, and thus reduce the vaccine cost during production Compared to the current aqueous rotavirus vaccines in the market, the vaccine formulation of the invention keeps the virus in a dried lyophilized micronized state. Lyophilizing the virus at high titer has the great advantage of reducing the footprint required to manufacture the vaccine from a commercial scale facility to a smaller pilot plant space. To begin manufacture, it is better to start with a high titer (8.2-8.3 $\log_{10}$ [FFU/mL]) of 116E rotavirus in IVT-06 formulation. Considering that one human dose (0.5 mL) of this new thermo-stable oral vaccine will contain a viral titer of 5.9 $\log_{10}$ [FFU/mL], then the lyophilized material of one liter (L) will produce about 150 L of liquid IVT-06 vaccine, or the equivalent of 300 thousand doses. Using a small 50 L Virtis freeze dryer and 10 L of the high titer IVT-06 formulation, this can be lyophilized to obtain an equivalent to 3 million doses produced per week and for 45 weeks per annum, to have a capacity of approximately 150 million doses. Lyophilization of these 10 L generates approximately one Kg of dried material, which can be easily micronized in the current jet mill in under 2 hours. A production capacity can be easily doubled to 300 million doses per year by using an extra freeze dryer of the same capacity.

The early development of a small volume, ready to use, thermo-stable oral rotavirus (attenuated) vaccine formulation with features that greatly broaden the efficacy of rotavirus vaccine program in countries that most need it. This vaccine is easily produced at current commercial scale levels in smaller production facilities. Preliminary results indicate that the titer loss associated with the transition of the freeze-dried material to a final liquid IVT-06 formulation is around 0.2 $\log_{10}$ [FFU/mL]. This is encouraging as this value is below the error for the FFA titer assay (+/−0.33 $\log_{10}$ [FFU/mL]) itself.

The following examples illustrate embodiments of the invention, but should not be viewed as limiting the scope of the invention.

EXAMPLES

Example 1 Rotavirus Strain and Chemical Reagents

The naturally attenuated asymptomatic human bovine reassortant rotavirus strain 116E (serotype G9P[11]) used in this development had ingredients like sodium chloride, monosodium glutamate, Tris base, sucrose, and sodium bicarbonate reagents obtained from Fisher Bioreagents. DMEM and MEM growth media was purchased from Corning Life Sciences (Tewksbury, Mass.). Trizma, Hepes buffer and L-Arginine were obtained from Sigma Aldrich Saint Louis, Mo. Sodium citrate anhydrous powder (ADM, Chicago, Ill.) and Sodium adipate was from TCI America (Portland, Oreg.). Although the examples refer to immunogenic compositions of attenuated Rotavirus, the formulations are applicable to other types of virus including, but not limited to the non-enveloped viruses such as norovirus, adenovirus, papilloma virus, and picornavirus, and the enveloped viruses, Hepatitis virus, Corona virus, Influenza virus, and rabies virus.

Example 2 Focus Fluorescent Assay (FFA) Development

This assay has been previously described (WHO/IVB/08.17 document, 2009) and was stablished with the following modifications. In brief, MA104 cells obtained from ATCC were grown in DMEM media (Gibco) with 10% FBS and seeded at 3.0E+04 cells per well in flat bottom 96-well plate(s) (Corning/Costar #3603) and allowed to grow for 36-48 hrs.

Lyophilized rotavirus samples were suspended in WFI with the original volumes dispensed in the vials previous to lyophilization. The rotavirus present in 0.1 mL of the suspended sample was activated for infectivity by diluting them with a 10 μg/mL trypsin solution in DMEM media without serum, and incubated for 30 min in a 37° C. water bath.

Rotavirus samples were then diluted 1:5 with warmed serum-free DMEM media, and then serially diluted 1:4 in 96-well plate(s) in the same media.

For infections, the MA104 cells present in the 96-well plate(s) were washed twice with 150 μl of serum-free DMEM media, and then incubated with 50 μL of the serially diluted rotavirus samples for 60 min at 37° C. with 5% $CO_2$ inside a tissue culture incubator. Virus was then diluted with the addition of 150 μL per well of serum-free DMEM media with 1 μg/mL of trypsin, and incubated as before for 18-19 hours.

Cells were fixed by removing the virus from the plate(s), washing each well with 150 μL of PBS, and then adding 150 μL of 80% acetone solution. The plate(s) were incubated for 5-10 min at room temperature (RT). Acetone was then discarded and the plate air dried for 30-60 min in the dark. The cells were hydrated with 50 μL of washing buffer [PBS with 0.05% Tween-20]per well for at least 5 min.

Fluorescent detection of rotavirus infective particles was performed by removing the hydrating solution and adding to each well 50 μL of anti-VP6 monoclonal antibody (GeneTex

GTX36628) diluted to 1 μg/mL in PBS buffer with 1% BSA. Plate(s) were incubated at 37° C. for 60 min, the antibody removed, and wells washed twice with washing buffer. 50 μL of goat anti mouse IgG (H+L) conjugated to Alexa 488 fluorophore (Thermo-Fisher #A-11001) was diluted 1:1000 in PBS plus 1% BSA solution was added to each well, and the plate(s) incubated at 37° C. for 60 min. Wells were then washed twice with washing buffer, stained for 10 min with 50 μL of 2 μM DAPI solution in PBS, washed once with 150 μL of PBS and WFI, and the plate(s) stored semi dried, wrapped in foil at 4-8° C. overnight.

Counting of fluorescent focus-forming units in each well was done by taking pictures for DAPI, Alexa-488, and transmitted light channels using a Zeiss Observer Z1 inverted microscope equipped with a Hamamatsu Orca ER CCD camera. Data analysis was done using the Cellomics high content analysis software suite (ThermoFisher Scientific) to determine the fluorescent focus units per mL in each well.

Example 3 Freeze Drying Process

Initial lyophilization of the factorial formulation screening in 96-well flat bottom plates (Corning-Costar #3603), and original analysis of lead formulations were done using a Virtis Genesis 25 L Pilot freeze dryer model EL, equipped with a Wizard 2.0 control system. This unit is outfitted with a hydraulic stoppering system and a lyophilization chamber containing three shelfs with temperature control ranges from minus 55° C. to 65° C.

Improvement of the conservative lyophilization cycle described herein, as well as lyophilization of lead IVT-05 and IVT-06 formulations done in vials, or bulk (2.0 L Lyogard trays) were done in a Virtis Ultra 50 L Pilot freeze dryer model EL (SP Scientific, Stone Ridge, N.Y.). This unit is equipped with 10 hydraulic shelfs for automatic stoppering, a Pirani vacuum valve, and is controlled with an Encore software control system.

Both freeze dryers were connected to high purity Nitrogen gas tanks (AirGas #NI HP300 CGA) to fill their chambers and maintain the lyophilized materials under inert atmosphere while stoppered.

Example 4 Differential Scanning Calorimetry (DSC) for Tg Determinations

All DSC data were collected using a TA Instruments 910 differential scanning calorimeter equipped with a high-sensitivity sample and control cells controlled by Instrument Specialists Inc. (ISI), and a Windows based data collection software. Data was analyzed using ISI's analysis program against a reference pan to generate the final thermograms.

In brief, the lyophilized cake's materials (15-20 mg in weight) were place in aluminum pan and heated from room temperature (e.g., 20° C.) to 100° C. at 4° C./min under dry nitrogen flow at a rate of 25 mL/min. Samples were held in covered aluminum pan for the duration of the testing.

Example 5 Accelerated Stability Studies

Five ml cGMP sterile and depyrogenized Daikyo Crystal Zenith ready pack vials (Afton Scientific Corp., Charlottesville, Va.) were used for lyophilization of all formulations that were tested for accelerated stability studies.

Vials were incubated at 30° C., 40° C. and/or 50° C. for different lengths of time in calibrated and validated Lab Line Imperial III incubators with digital temperature controls, and equipped with digital temperature data loggers.

Portions of the vials from each of the lyophilization batches were also stored immediately after lyophilization at minus 80° C. freezer and used as controls (time zero). Every week or month, vials were removed from different incubators, and together with the time zero vial controls, subjected to rotavirus viral titer estimations using a focus fluorescent assay. At least two vials per sample were used for titer determinations. The login of viral titers [FFU/mL] were subtracted from the original time zero control to evaluate the titer loss at each data point.

Example 6 Baby Rossett-Rice (BRR) Assay for Buffering Capacity Evaluation

Procedure for BRR Assay: A 500 mL beaker containing 50 mL of distilled water was used as a 37° C. water bath by placing it on top of a temperature controlled digital stirrer and plate heater (Corning, model PC620D). Once the water bath reached temperature, a 50 ml reaction beaker containing a small magnetic stirrer and 9.5 mL of water for injection (WFI) was placed inside the water bath, stirred at 100 rpm/min and incubated for 5 minutes until its temperature reached 37° C. A constant 0.5 mL volume of full IVT-06 formulation suspension (equivalent to one human vaccine dose) containing milled buffering agents and milled IVT-06 formulation (<5 μm particle size) in MCT was added to the 9.5 mL in the reaction vessel to assess the buffering capacity of different buffer combinations. The initial pH in the reaction beaker was measured and recorded (time zero) with a previously calibrated (pH standards 4.0; 7.0, and 10.0) Orion A215 pH-meter equipped with a micro pH probe. Immediately thereafter, 4.0 mL of 0.1N hydrochloric acid was added, and at the same time, a Baxter model PCAII infusion pump that has been previously calibrated, was used to start adding to the reaction beaker 0.1N Hydrochloric acid at a rate of 0.5 mL/minute. A stop watch was used to record the pH values of the reaction beaker every minute for 30 minutes, after which, the clock and pump were stopped. Each buffering capacity evaluation was done in triplicate. The average data points with their respective standard deviations were used for the buffering capacity analysis.

Example 7 Jet Milling and Final Formulation Preparation

A two inch Micron Master Jet Pulverizer model 02-612c-SS-SAN (The Jet Pulverizer Co., Moorestown, N.J.) was used to micronize the lead IVT-06 lyophilized rotavirus formulation and buffering components (less than or equal to 5 μm particle size). The jet mill is equipped with a Schenck AccuRate model 106 feeder (Schenck Process GmbH, Darmstadt, Germany) to accurately control the feeding rate of materials during micronization. The mill was enclosed inside a custom-designed 4×3×4 feet glove box containing input and output ports facilitating the filling of the glove box with high purity Nitrogen gas with the goal of milling under low moisture conditions. Moisture inside the glove box was measured with a calibrated digital hand-held hygrometer (TPI Inc., Beaverton, Oreg.), and milling was started only when the relative humidity inside the box was less than 5%. Also used was a Draeger PAC5500 oxygen gas monitoring system (Draegger, Pittsburgh, Pa.) to control the oxygen levels in the milling room while the mill was operational.

Disposable Lyogard trays (GORE; Newark, Del.) were used to lyophilized bulk placebo IVT-06 formulation. Immediately after lyophilization, a tray was brought inside the nitrogen-filled, low-moisture glove box and the dried IVT06 material passed through an 18 mesh T316 stainless steel sieve to load homogeneous dried formulation into the feeder. The placebo was used to calibrate and obtain the optimal feeder rate to micronize the IVT-06 formulation to a particle size below 5 μm in diameter during the jet milling process. Similar processes were performed for the buffering system composed of a mix of sodium citrate and calcium carbonate salts.

During micronization, the jet mill was connected to a custom-made in-line nitrogen gas tank system designed to deliver high purity gas at a minimum of 100 psi of pressure, and 20 scfm of gas flow. Micronized material was collected in a 10 L stirred T316 stainless steel product receiver attached to the mill through a tri-clover clamp connection. Samples were taken and suspended in a test tube containing MCT. Particle size analyses of the suspensions were done using a Zeiss Axiolab microscope equipped with 100× oil immersion objective, phase polarization filters, and a CCD camera. Pictures of the milled suspension were taken at different magnifications and particle size estimated using the ZEN digital imaging software.

On occasions when there was leftover micronized material, it was stored in vacuumed food-storage bags containing two dry-silica gels sachets inside to preserve low moisture conditions. Bags were stored under vacuum in container with Drierite pellets (Sigma Aldrich) either at room temperature or 4° C.

The final vaccine formulation (0.5 mL per human dose) was prepared inside the low moisture glove box by combining 120 mg of milled IVT-06 formulation containing the 116E rotavirus, and 65.0 mg of milled buffering agents in a final volume of 0.5 mL of MCT oil. The mix was fully homogenized in a glass beaker by stirring it at 150 rpm/min for 30 min before it was dispensed into sterile GMP grade glass vials. Vials were flushed with nitrogen gas before they were closed with rubber stoppers and clamped with aluminum seals.

Example 8 IVT-06 Formulations

Formulations of vaccines of the disclosure were generated. Vaccines were composed of the ingredients listed in Table 1.

TABLE 1

(IVT-06)

| Ingredient | Concentration |
|---|---|
| Hepes Buffer | 50 mM |
| Sucrose | 7.35% (w/v) |
| L-arginine | 230 mM (4% w/v) |
| NaCl | 30 mM (1.76% w/v) |
| pH | 7.2 ± 0.2 |
| Glass temp. Tg | 77.6° C. ± 1.0 |
| Moisture | ≤1.2% |
| Dissolution time | 10 ± 5 secs. |
| Solids content | 140 g/L (after lyophilization) |

Jet milling of the lyophilized IVT-06 formulation using a customized micron master jet pulverizer, model 02-012c-SAN-SS) located inside a glove box, in nitrogen atmosphere and at room temperature. Milling start only when the RH % is <5%. Particle size D90< of equal to 5 μm. Maltodextrin was not used. Particle size of IVT was less than 5 microns making it suitable for infants without any need for dissolving. Additional formulations were created with the same components, but with varying concentrations of sucrose and L-arginine. Arginine to sucrose rations tested were from about 1 to about 1.2-1.9. An acceptable stability was achieved for all ratios tested. Arginine to sucrose ratios of 1:1.1, 1:1.2, 1:1.25, 1:1.3, 1:1.4, 1:1.5, 1:1.6, 1:1.7, 1:1.8, 1:1.9, 1:2, 1:2.1, 1:2.2, 1:2.3, 1:2.4, 1:2.5 and greater are preferred. The Tg of various formulations disclosed herein is 65° C. or greater, 70° C. or greater, 75° C. or greater, 80° C. or greater, 85° C. or greater, or 90° C. or greater.

Example 9 Real Time Stability

IVT-06 formulations were tested for stability 2% or 4% arginine with 116E Rotavirus. The initial virus titer was ~4.5 log 10 [FFU/mL] with lyophilization at 1 mL in 5 mL glass vials. Results are shown in Table 2A and Table 2B.

TABLE 2A

| IVT-06 with 2% L-Arginine |
|---|
| 30° C. +/− 2° C.: at least 2 years. |
| Expected to be stable >3 years with less than 0.3 log10 [FFU/mL] titer loss. |
| 40° C. +/− 2° C.: at least 19 months with 0.5 log10 [FFU/mL] titer loss |

TABLE 2B

| IVT-06 with 4% L-Arginine |
|---|
| 30° C. +/− 2° C.: at least 24 months. |
| Expected to be stable >3 years with less than 0.5log10 [FFU/mL] titer loss. |
| 40° C. +/− 2° C.: at least 24 months with 0.5log10 [FFU/mL] titer loss. |
| 50° C. +/− 2° C.: at least 3 months without titer loss. |

Linear regression analysis predicts stability of IVT-06 with 4% L-Arginine for 5 mos. at 50° C. with titer loss of 0.5 log 10 [FFU/mL]. These results indicate that IVT is stable, and without the need for additional ingredients, at 30° C. for at least 1,095 days, at 40° C. for at least 365 days and at 50° C. for at least 150 days. Total solids are high in IVT formulation as compared to conventional formulations. Dissolution time for IVT was 10 seconds, Tg value, which indicates stability, for IVT was 77.6° C., moisture is sufficient of supportive environment for virus stability at less than 1.2%, with dissolution time to administration to infants without a risk of choking.

Example 10 Rotavirus Stabilities

Formulations tested contained the same amount of sucrose and either o %, 2%, or 4% arginine (see Table 3).

TABLE 3

Rotavirus stability with different Amino acid concentrations

| Formulation | Glass Transition Temperature (Tg) | Stability at 40° C. (months) | Stability at 50° C. (months) |
|---|---|---|---|
| IVT-06 without L-Arg | 49.4° C. ± 1° C. | 0.5 | ≤0.5 |
| IVT-06 with 2% L-Arg (w/v) | TBD | 19 | 1 |
| IVT-06 with 4% L-Arg (w/v) | 77.6° C. ± 1° C. | ≥24 | ≥3 |

Increases L-Arginine concentrations in the formulation increases the Tg. Increases of Tg increases the formulation stability at higher temperatures. The Tg value for the IVT-06 without Arginine formulation (49.4° C.+/−1° C.) is based on the stability presented in the table above and the similarity of Tg values.

Other embodiments and uses of the invention will be apparent to those skilled in the art from consideration of the specification and practice of the invention disclosed herein. All references cited herein, including all publications, and all U.S. and foreign patents and patent applications are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. An immunogenic composition comprising:

an attenuated strain of a rotavirus at a titer of about $10^{5.9}$ FFU/mL or higher;

arginine and sucrose at a ratio of from about 1:1.1-2.5;

less than or equal to about 1.2% moisture;

an approximate uniform particle size of about 5 μm or less;

a buffering agent; and medium-chain triglyceride (MCT).

2. The composition of claim 1, wherein the rotavirus includes one or more serotypes of rotavirus.

3. The composition of claim 1, which comprises approximately 2-4% arginine (w/v).

4. The composition of claim 1, which comprises approximately 4-6% arginine (w/v).

5. The composition of claim 1, which comprises approximately 6-8% sucrose (w/v).

6. The composition of claim 1, which comprises approximately 8-10% sucrose (w/v).

7. The composition of claim 1, wherein the ratio of from about 1:1.1-2.0.

8. The composition of claim 1, wherein the ratio of from about 1:1.1-1.75.

9. The composition of claim 1, wherein the buffering agent comprises a mix of citrate and calcium carbonate, Tris, Hepes, phosphates, histidine, or a combination thereof.

10. The composition of claim 1, wherein the buffering agent maintains the composition at a pH of about 7.0-8.0.

11. The composition of claim 1, which is lyophilized.

12. The composition of claim 1, which as a glass transition temperature of about 70° C. or higher.

13. The composition of claim 1, which as a glass transition temperature of about 75° C. or higher.

14. The composition of claim 1, which as a glass transition temperature of about 80° C. or higher.

15. The composition of claim 1, which, when stored at about room temperature or higher for at least about twelve months, has no significant loss of efficacy.

16. The composition of claim 1, which, when stored at about 30° C. or higher for at least about two years, has no significant loss of efficacy.

17. The composition of claim 1, which, when stored at about 50° C. or higher for at least about six months, has no significant loss of efficacy.

18. The composition of claim 1, which, when stored at about 50° C. or higher for at least about twelve months, has no significant loss of efficacy.

19. An immunogenic composition comprising:

an attenuated strain of a rotavirus at a titer of about $10^{5.9}$ FFU/mL or higher;

less than or equal to about 1.2% moisture;

an approximate uniform particle size of about 5 μm or less;

a buffering agent; and medium-chain triglyceride (MCT), wherein the composition has a glass transition temperature of about 60° C. or higher.

20. The composition of claim 19, wherein the rotavirus includes one or more serotypes of rotavirus.

21. The composition of claim 19, which comprises approximately 2-4% arginine (w/v).

22. The composition of claim 19, which comprises approximately 4-6% arginine (w/v).

23. The composition of claim 19, which comprises approximately 6-8% sucrose (w/v).

24. The composition of claim 19, which comprises approximately 8-10% sucrose (w/v).

25. The composition of claim 19, arginine and sucrose at a ratio of from about 1:1.1-2.5.

26. The composition of claim 25, wherein the ratio of from about 1:1.1-1.75.

27. The composition of claim 19, wherein the buffering agent comprises a mix of citrate and calcium carbonate, Tris, Hepes, phosphates, histidine, or a combination thereof.

28. The composition of claim 19, wherein the buffering agent maintains the composition at a pH of about 7.0-8.0.

29. The composition of claim 19, which is lyophilized.

30. The composition of claim 19, which as a glass transition temperature of about 70° C. or higher.

31. The composition of claim 19, which as a glass transition temperature of about 75° C. or higher.

32. The composition of claim 19, which as a glass transition temperature of about 80° C. or higher.

33. The composition of claim 19, which, when stored at about room temperature or higher for at least about twelve months, has no significant loss of efficacy.

34. The composition of claim 19, which, when stored at about 30° C. or higher for at least about two years, has no significant loss of efficacy.

35. The composition of claim 19, which, when stored at about 50° C. or higher for at least about six months, has no significant loss of efficacy.

36. The composition of claim 19, which, when stored at about 50° C. or higher for at least about twelve months, has no significant loss of efficacy.

* * * * *